United States Patent [19]

Tan et al.

[11] Patent Number: 4,886,912

[45] Date of Patent: Dec. 12, 1989

[54] CYANOGUANIDINE DERIVATIVE AND PROCESS FOR PREPARATION THEREOF

[75] Inventors: Hiroaki Tan, Otake; Keiichi Yokoyama; Noriaki Kihara, both of Iwakuni, all of Japan

[73] Assignee: Mitsui Petrochemical Industries, Ltd., Tokyo, Japan

[21] Appl. No.: 156,668

[22] Filed: Feb. 17, 1988

[30] Foreign Application Priority Data

Feb. 17, 1987 [JP] Japan ................................. 62-32329

[51] Int. Cl.$^4$ ........................................... C07C 129/08
[52] U.S. Cl. .................................................. 564/240
[58] Field of Search ......................................... 564/240

[56] References Cited

U.S. PATENT DOCUMENTS 4,276,421 6/1981 Baudet ................................. 564/240

FOREIGN PATENT DOCUMENTS 455991 2/1978 Spain ................................... 564/240

Primary Examiner—James H. Reamer
Attorney, Agent, or Firm—Sherman and Shalloway

[57] ABSTRACT

The present invention provides a cyanoguanidine derivative which is a precursor for the synthesis of N-cyano-N'-methyl-N"-[2-{(5-methyl-1H-imidazol-4-yl)methylthio}ethyl]-guanidine (Cimetidine) or its related compound, which has an action of controlling secretion of acid in the stomach based on the histamine $H_2$ receptor antagonism and is valuable as a drug for treating gastric ulcer. This cyanoguanidine derivative is prepared by reacting other cyanoguanidine derivative with a halogenating agent.

2 Claims, No Drawings

CYANOGUANIDINE DERIVATIVE AND PROCESS FOR PREPARATION THEREOF

BACKGROUND OF THE INVENTION

(1) Field of the Invention

The present invention relates to a precursor for the synthesis of Cimetidine which has an action of controlling secretion of acid in the stomach based on the histamine $H_2$ receptor antagonism and is valuable as a drug for treating gastric ulcer, and a process for the preparation of this precursor.

(2) Description of the Prior Art

Imidazole derivatives such as 4-hydroxymethyl-5-methylimidazole disclosed in Japanese Patent Application Laid-Open Specification No. 142271/81, 4-(2-aminoethylthio)-5-methylimidazole disclosed in Japanese Patent Application Laid-Open Specification No. 42661/72 and [(4-methyl-5-imidazolyl)methylthioethyl]-S-methylisothiourea are mainly known as the precursor for the synthesis of Cimetidine, and Cimetidine can be derived from these imidazole derivatives. As the precursor that can be converted to Cimetidine by forming an imidazole ring at the final stage, there can be mentioned N-cyano-N'-2-(2,3-diketobutylthio)ethyl-N''-methylguanidine disclosed in Spanish Patent No. 455,991 [Chemical Abstracts, 89, 146904 I, 1978]. Diacetyl which is the starting material for the synthesis of this precursor has an offensive smell and causes a problem concerning the working environment, and the yield of the precursor is not always high.

SUMMARY OF THE INVENTION

We made investigations with a view to developing a reasonable Cimetidine-preparing process having a reduced number of reaction stages and simplifying operations. As the result, we found a novel cyanoguanidine derivative which is quite different from the above-mentioned compounds disclosed in the literature references. Accordingly, the present invention provides this novel cyanoguanidine derivative and a process for the preparation of this novel cyanoguanidine derivative.

This cyanoguanidine derivative can be easily converted to Cimetidine, for example, by reacting the cyanoguanidine derivative in ethanol at room temperature in the presence of formalin and aqueous ammonia.

More specifically, the present invention relates to a novel cyanoguanidine derivative and a process for the preparation thereof. The novel cyanoguanidine derivative is represented by the following formula (I):

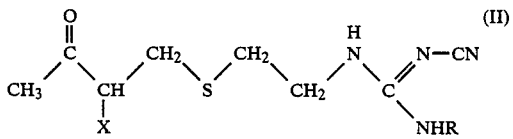

wherein X and Y, which may be the same or different, stand for a chlorine atom or a bromine atom, and R stands for an alkyl group.

The cyanoguanidine derivative of the formula (I) according to the present invention can be prepared by reacting a cyanoguanidine derivative represented by the following formula (II):

wherein X and R are as defined above, with a halogenating agent.

The cyanoguanidine derivative (haloketone derivative) of the formula (II), which is used as the starting material in the above reaction, can be prepared, for example, according to the process disclosed in our copending Japanese Patent Application No. 203640/86, which comprises reacting a methylvinylketone represented by the following formula (III):

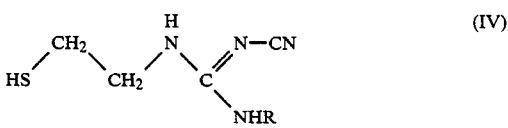

wherein X stands for a hydrogen atom, a chlorine atom or a bromine atom, with a mercaptoguanidine derivative represented by the following formula (IV):

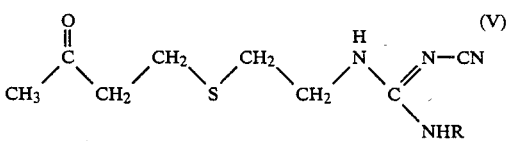

wherein R stands for a lower alkyl group, or reacting an amidinoketone derivative represented by the following formula (V):

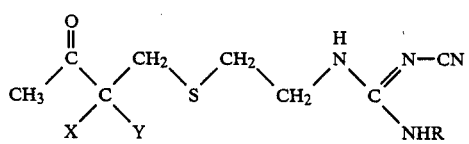

wherein R stands for a lower alkyl group, with a halogenating agent.

The methylvinylketone derivative of the formula (III) can be easily obtained by dehydrohalogenating a compound represented by the following formula:

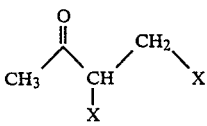

in the presence of a base.

DETAILED DESCRIPTION OF THE PREFERRED EMBODIMENTS

The novel cyanoguanidine derivative of the present invention is represented by the above-mentioned general formula (I), and in the general formula (I), X and Y, which may be the same or different, stand for a chlorine atom or a bromine atom, and R stands for a lower alkyl group such as a methyl group, an ethyl group or an n-propyl group.

Examples of the compound of the present invention are described below.

| Compound No. | X | Y | Z |
| --- | --- | --- | --- |
| 1 | Cl | Cl | Me |
| 2 | Cl | Br | Me |
| 3 | Br | Br | Me |
| 4 | Cl | Cl | Et |
| 5 | Cl | Br | Et |

The novel cyanoguanidine derivative represented by the general formula (I) is synthesized by halogenating the compound represented by the general formula (II).

As the halogenating agent, there can be mentioned chlorine, bromine, sodium hypochlorite, calcium hypochlorite (bleaching powder), potassium hypochlorite and t-butyl hypochlorite.

In the case where chlorine or bromine is used as the halogenating agent, the halogenation is carried out at −70° to 50° C. for 0.1 to 5 hours by using a solvent in an amount of 100 ml to 10 l, preferably 1 to 5 l, a basic catalyst in an amount of 1 to 100 moles and the halogenating agent in amount of 1 to 100 moles, preferably 1 to 10 moles, per mole of the compound of the formula (II). More preferably, the halogenation is carried out at 0° to 30° C. for 0.1 to 2 hours. As preferred examples of the solvent used singly, there can be mentioned halogenated lower alkyl compounds such as chloroform, methylene chloride and dichloroethane and ethers such as diethyl ether and dioxane. As the basic catalyst, there can be used trialkylamines such as triethylamine, trimethylamine and triisopropylamine and pyridines such as pyridine and 4-N,N-dimethylaminopyridine.

In the case where sodium hypochlorite, calcium hypochlorite, potassium hypochlorite or t-butyl hypochlorite is used as the halogenating agent, the halogenation is carried out at −20° to 50° C., preferably 0° to 30° C., for 0.1 to 5 hours, preferably 0.1 to hours, by using a solvent in an amount of 100 ml to 10 l, preferably 1 to 5 l, and the halogenating agent in an amount of 1 to 10 moles, preferably 1 to 3 moles, per mole of the compound of the formula (II). As the solvent, there can be used lower alcohols such as methanol, ethanol, n-propanol and isopropanol, halogenated lower alkyl compounds such as chloroform and methylene chloride, ether solvents such as diethyl ether and dioxane and ester solvents such as ethyl acetate.

After the reaction, the intended compound is isolated by adding water to the reaction mixture, extracting the mixture with an organic solvent such as chloroform or ethyl acetate and subjecting the extract to ordinary refining means such as column chromatography.

The cyanoguanidine derivative of the general formula (I) obtained according to the present invention can be easily converted to Cimetidine, for example, by reacting the cyanoguanidine derivative of the formula (I) in ethanol at room temperature in the presence of formalin and aqueous ammonia according to the invention of our copending Japanese Patent Application No. 32327/87 entitled "PROCESS FOR PREPARATION OF IMIDAZOLE DERIVATIVES".

The present invention will now be described in detail with reference to the following examples and referential examples.

EXAMPLE 1

Preparation of N-[2-(2-bromo-2-chloro-3-oxobutylthio)]-ethyl-N'-cyano-N''-methylguanidine (compound 2)

In 1 ml of methylene chloride was dissolved 0.13 g of N-[2-(2-chloro-3-oxobutylthio)]ethyl-N'-cyano-N''-methylguanidine and 1 ml of triethylamine, and a solution of 0.25 g of bromine in 2.5 ml of methylene chloride was added dropwise to the above solution while maintaining the temperature at 10° to 20° C. The mixture was stirred at 20° C. for 30 minutes, and a saturated aqueous solution of sodium hydrogencarbonate and ethyl acetate were added to the mixture to effect extraction. The organic layer was dried with anhydrous sodium sulfate and concentrated under reduced pressure. The obtained residue was refined by silica gel column chromatography (developing solvent: ethyl/ethanol=10/1) to obtain 82 mg of a colorless oily product (the yield 48%).

$^1$H-NMR(in CDCl$_3$, δ ppm)

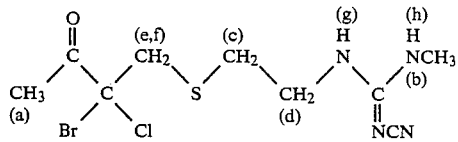

(a) 2.61 (3H, s), (b) 2.90 (3H, d, J=6 Hz), (c) 2.91 (2H, t, J=7 Hz), (d) 3.47 (2H, q, J=7 Hz), (e) 3.48 (1H, d, J=14 Hz), (f) 3.72 (1H, d, J=14 Hz), (g) 5.80 (1H, br.t), (h) 6.08 (1H, br.q).

EXAMPLE 2

Preparation of N-cyano-N'-[2-(2,2-dichloro-3-oxobutylthio)]ethyl-N''-methylguanidine (compound 1)

In 1 ml of methanol was dissolved 131 mg of N-[2-(2-chloro-3-oxobutylthio)]ethyl-N'-cyano-N''-methylguanidine, and 0.63 ml of an aqueous solution of sodium hypochlorite was added to the solution and reaction was carried out at room temperature for 3 hours. Then, 15 ml of ethyl acetate was added to the reaction liquid and the organic layer was recovered. The obtained organic layer was dried with anhydrous sodium sulfate and concentrated under reduced pressure. The obtained residue was refined by silica gel column chromatography (developing solvent: ethyl/ethanol=10/1) to obtain 37 mg of a colorless oily product (the yield was 25%).

$^1$H-NMR(in DC$_3$OD, δ ppm)

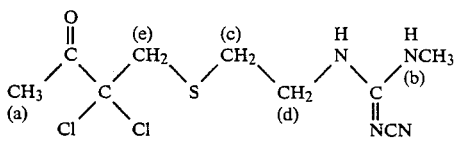

(a) 2.56 (3H, s), (b) 2.84 (3H, s), (c) 2.86 (2H, t, J=7 Hz), (d) 3.41 (2H, t, J=7 Hz), (e) 3.56 (2H, s).

EXAMPLE 3

Preparation of N-cyano-N'-[2-(2,2-dichloro-3-oxobutylthio)]ethyl-N''-methylguanidine In 1 ml of methanol was dissolved 131 mg of N-[2-(2-chloro-3-oxobutylthio)]ethyl-N'-cyano-N''-methylguanidine, and the solution was cooled with water and 55 mg of t-butyl hypochlorite was added to the solution.

The mixture was stirred at 0° C. for 1 hour and 1 ml of water and 15 ml of ethyl acetate were added to the reaction mixture. The ethyl acetate layer was recovered, dried with anhydrous sodium sulfate and concentrated under reduced pressure. The obtained residue was refined by silica gel column chromatography (developing solvent: ethyl acetate/ethanol=10/1) to obtain 24 mg of a colorless oily product (the yield was 16%).

REFERENTIAL EXAMPLE 1

Preparation of N-cyano-N'-methyl-N''-[2-{(5-methyl-1H-imidazol-4-yl)methylthio}ethyl]guanidine (Cimetidine)

In 1 ml of methanol was dissolved 149 mg of N-cyano-N'-[2-(2,2-dichloro-3-oxobutylthio)]ethyl-N''-methylguanidine, and 0.5 ml of aqueous ammonia (ammonia content=28%) and 0.06 ml of formalin (formaldehyde content=37%) were added to the solution and the mixture was stirred at room temperature for 20 hours. The solvent was removed from the reaction mixture under reduced pressure, and the obtained residue was refined by silica gel column chromatography (eluting solvent: MeOH/CHCl$_3$=1/20-→MeOH/CHCl$_3$=1/10) to obtain 36 mg of intended Cimetidine (the yield was 28%).

REFERENTIAL EXAMPLE 2

Preparation of N-cyano-N'-methyl-N''-[2-{(5-methyl-1H-imidazol-4-yl)methylthio}ethyl]guanidine (Cimetidine)

In 1 ml of methanol was dissolved 171 mg of N-2-(2-bromo-2-chloro-3-oxobutylthio)ethyl-N'-cyano-N''-methylguanidine, and the solution was cooled with water and 0.5 ml of aqueous ammonia (ammonia content=28%) and 0.06 ml of formalin (formaldehyde content=37%) were added to the solution. The mixture was stirred at room temperature for 1 hour and the solvent was removed under reduced pressure. The obtained residue was refined by silica gel column chromatography (eluting solvent: MeOH/CHCl$_3$=1/20-→MeOH/CHCl$_3$=1/10) to obtain 30 mg of intended Cimetidine (the yield was 24%).

We claim:

1. A cyanoguanidine derivative represented by the following general formula (I):

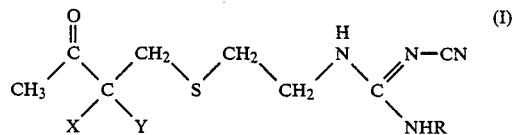

wherein X and Y, which may be the same or different, stand for a chlorine atom or a bromine atom, and R stands for a lower alkyl group.

2. A cyanoguanidine derivative as set forth in claim 1, wherein in the general formula (I), R is a lower alkyl group selected from the group consisting of a methyl group, an ethyl group and an n-propyl group.

* * * * *